(12) United States Patent
Auton

(10) Patent No.: US 8,980,566 B2
(45) Date of Patent: Mar. 17, 2015

(54) BIOMARKERS FOR RESPIRATORY INFECTION

(71) Applicant: Aseptika Ltd, Huntingdon, Cambridgeshire (GB)

(72) Inventor: Kevin Andrew Auton, Huntingdon (GB)

(73) Assignee: Aseptika Ltd, Cambridgeshire (GB)

( * ) Notice: Subject to any disclaimer, the term of this patent is extended or adjusted under 35 U.S.C. 154(b) by 0 days.

(21) Appl. No.: 14/345,994

(22) PCT Filed: Sep. 19, 2012

(86) PCT No.: PCT/GB2012/052307
§ 371 (c)(1),
(2) Date: Mar. 20, 2014

(87) PCT Pub. No.: WO2013/041854
PCT Pub. Date: Mar. 28, 2013

(65) Prior Publication Data
US 2014/0227716 A1    Aug. 14, 2014

(30) Foreign Application Priority Data

Sep. 20, 2011 (GB) .................................. 1116234.4
Jul. 23, 2012 (GB) .................................. 1213025.8

(51) Int. Cl.
*G01N 33/53* (2006.01)
*G01N 33/569* (2006.01)
*G01N 21/64* (2006.01)
*C12Q 1/04* (2006.01)

(52) U.S. Cl.
CPC ...... *G01N 33/56911* (2013.01); *G01N 21/6428* (2013.01); *C12Q 1/04* (2013.01); *G01N 2021/6421* (2013.01); *G01N 2333/21* (2013.01)
USPC ............................................. 435/7.1; 435/7.2

(58) Field of Classification Search
None
See application file for complete search history.

(56) References Cited

U.S. PATENT DOCUMENTS

2005/0119302 A1* 6/2005 Rahme et al. ................. 514/312

FOREIGN PATENT DOCUMENTS

GB           2494953 B      9/2013
WO    WO 2006/000056 A1    1/2006

OTHER PUBLICATIONS

Haas, B. et al., "Siderophore Presence in Sputa of Cystic Fibrosis Patients," Infection and Immunity 59(11):3997-4000 (1991).
Jaffar-Bandjee, M.C. et al., "Production of Elastase, Exotoxin A, and Alkaline Protease in Sputa during Pulmonary Exacerbation of Cystic Fibrosis in Patients Chronically Infected by *Pseudomonas aeruginosa*," J. of Clinical Microbiology 33(4):924-929 (1995).
Karpati, F. et al., "TNF-α and IL-8 in Consecutive Sputum Samples from Cystic Fibrosis Patients During Antibiotic Treatment," Scand. J. Infect. Dis. 32:75-79 (2000).
Martin, L.W. et al., "*Pseudomonas* siderophores in the sputum of patients with cystic fibrosis," Biometals 24:1059-1067 (2011).
Rogers, G.B. et al., "Using bacterial biomarkers to identify early indicators of cystic fibrosis pulmonary exacerbation onset," Expert Rev. Mol. Diagn. 11(2):197-206 (2011).
Tramper-Stranders, G.A. et al., "Diagnostic value of serological tests against *Pseudomonas aeruginosa* in a large cystic fibrosis population," Thorax 61:689-693 (2006).
International Patent Application No. PCT/GB2012/052307, International Search Report and Written Opinion dated Dec. 18, 2012.
International Patent Application No. PCT/GB2012/052307, International Preliminary Report on Patentability dated Apr. 3, 2014.
International Search Report and Written Opinion dated Dec. 18, 2012 for corresponding International Patent Application No. PCT/GB2012/052307.

* cited by examiner

*Primary Examiner* — Jacob Cheu
(74) *Attorney, Agent, or Firm* — Kilpatrick Townsend & Stockton LLP

(57) ABSTRACT

Methods of determining levels of activity of bacteria in the lungs of patients are described, in which levels of a marker of a bacterial iron scavenging processes (for example, siderophores) and levels of a secreted bacterial protein are measured over time. Changes in the measured levels over time allow levels of bacterial activity to be determined, and exacerbations of bacterial infection to be predicted and/or monitored. Additional markers may also be used. The methods of the invention may also be used for monitoring effectiveness of antibiotic treatment of lung infection. The invention is particularly useful for monitoring *P. aeruginosa* levels in lungs of cystic fibrosis patients. Kits for use in the methods are also described.

18 Claims, 10 Drawing Sheets

Well • F14
Lambda at Maximum 322.00

Well • E2
Lambda at Maximum 300.00

BIOMARKERS FOR RESPIRATORY INFECTION

CROSS-REFERENCE TO RELATED APPLICATIONS

This application is a national phase application of International PCT Application No. PCT/GB2012/052307, filed Sep. 19, 2012, which claims priority to Great Britain Patent Application No. 1116234.4, filed Sep. 20, 2011, and Great Britain Patent Application No. 1213025.8, filed Jul. 23, 2012. The disclosure of Great Britain Patent Application Nos. 1116234.4 and 1213025.8 are incorporated herein by reference in its entirety.

FIELD OF THE INVENTION

The present invention relates to a method for determining a level of activity of bacteria in the lung of a patient. The method is intended particularly, but not exclusively, for identifying the presence and level of activity of bacterial infection in the lung of patients with cystic fibrosis; or for predicting the exacerbation of an infection in such patients. Other aspects of the invention relate to methods for determining the effectiveness of a treatment of a bacterial lung infection.

BACKGROUND TO THE INVENTION

In the East of England region, 80,000-125,000 hospital bed days are required to treat patients with respiratory infections each year. The most challenging patients to treat are the most vulnerable: the elderly, neonates and those suffering from chronic conditions such as cystic fibrosis (CF), Chronic Obstructive Pulmonary Disease (COPD) or HIV. Respiratory infections in patients with chronic disease conditions can be difficult to treat: infection with even the most common respiratory pathogens may prove fatal.

Many patients with CF are colonised with one or more pathogens, the most common being *Pseudomonas aeruginosa*. This gram-negative bacterium colonises CF patients and evades all attempts at eradication. It undergoes numerous flare-ups (exacerbations) and the inflammation it causes results in the permanent loss of lung function. It also becomes resistant to antibiotics over time, making each subsequent infection more difficult to control than the last. This is an adaptable, resilient and lethal pathogen to be colonised with. The challenge for clinicians treating CF patients is to reduce the number of infections and decrease the severity of each infection. In doing so, lung function is preserved and life expectancy is increased. For most CF patients, a lung infection with the resulting sepsis and multiple organ failure, is the primary cause of death.

Infection with *P. aeruginosa* becomes problematic when there is an exacerbation of infection, triggered by other factors. If not treated promptly and with the correct antimicrobial medication, the patient may be admitted to hospital for 2-4 weeks until the infection can be controlled. This exacerbation and the lung inflammation which follows can be accompanied by a dramatic and often permanent loss of lung function and the rise in exotoxins produced by the pathogen, leading to sepsis.

At every stage in the treatment of infections, CF patients must travel to their clinic and see their clinician as an outpatient for several consultations. Failure to control infection as an outpatient results in a long-stay admission. Continued failure to control the frequent infections (a CF patient may suffer 4-6 infections a year), will cause irreparable damage to health which again, increases the cost of healthcare over the life-time of the patient.

It is important to note that it is not merely the presence of an infection which is adverse to patients. Many patients will have an ongoing, low level, infection which is subject to periodic exacerbations. Predicting the timing of these exacerbations is significant for management of treatment. Simply detecting the presence or absence of bacteria—for example, by nucleic acid sequencing—will not in itself be informative as to the likelihood of an exacerbation, as exacerbations can be triggered by many factors.

It is known to use the presence of a biomarker, such as a secreted protein, as a diagnostic for infection. For example, we have previously developed a simple laboratory-based test to measure *P. aeruginosa* Exotoxin A (a well known marker of infection by *P. aeruginosa*) in the patient's sputum.

But relying on a single biomarker for accurate assessment of the status of infection is problematic. For example, products which detect other pathogens often only look for toxins, such as the many rapid tests for *C. difficile* that are already on the market. These detect the presence of bacterial Toxins A and B in faecal samples. While quick to perform (30 minutes), these rapid tests have low accuracy because toxins A and B may not be produced during all infections or cannot be detected in a given sample—this gives a low detection rate compared with the slower, but more sensitive methods of culturing cells from a sample by traditional microbiology (2-3 days). Furthermore, it is believed that bacterial populations may alter the profile of toxins or other proteins produced over time in response to environmental factors; within a given population, there may be only some cells which produce a particular protein while the remaining cells contribute to the infection but rely on these exogenous proteins for their survival. It is also known that a given population of bacteria in a colonised patient mutate over time from the wild type with which the host was originally infected. Accordingly, detecting a single protein may not be sufficiently accurate as a diagnostic of the likelihood of an exacerbation.

To avoid this risk of poor accuracy, we have identified in the present invention several biomarkers which can be measured quantitatively. In addition, we can also profile biomarkers that indicate the status of the host's response to this pathogen. We believe that taken together, a combination of these markers can be used to detect an exacerbation before the patient feels unwell, thereby reducing the time to prescribe the first antibiotic and therefore reducing the severity of infection.

Martin et al., Biometals (2011) 24: 1059-1067 describes the detection of siderophores produced by *Pseudomonas aeruginosa* in the sputum of patients with cystic fibrosis. They found an association between presence of pyoverdine and number of bacteria, but not in 21 out of 148 patients; and conclude that there is no correlation between the amount of bacteria and clinical status. The authors also conclude that the levels of siderophores do not markedly change during exacerbations. This publication therefore teaches that profiling with siderophores cannot be used to determine the level of virulence.

By contrast, as described further below, the present inventors have determined that siderophores are a useful marker for bacterial exacerbations, when used in combination with other markers. We therefore provide an accurate and rapid test for determining such exacerbations.

Jaffar-Bandjee et al., Journal of Clinical Microbiology, April 1995, p 924-929 describes the production of elastase, exotoxin A, and alkaline protease in sputa during pulmonary exacerbation of CF in patients chronically infected by

*Pseudomonas aeruginosa*. They found that the concentrations of exoproteins varied by patient on admission (that is, after the exacerbation begins), but that the three proteins studied (elastase, Exotoxin A and alkaline protease) had similar levels. However, it is apparent from data presented in the current application that different patients may include different bacterial populations which produce different toxins or markers. Further, no test was made to detect exoprotein levels prior to exacerbations. Therefore profiling any of these exoproteins either alone or in combination will not provide sufficient data to predict all exacerbations in all CF patients.

Further, with an objective and quantitative test, the treating clinician will be able to quickly determine the performance of an antimicrobial medication in controlling the infection, substituting one antibiotic for another if the first fails to bring the infection under control. Typically, it can take up to 3 weeks to try different antibiotic combinations in an iterative process, before an effective solution is established—this is usually achieved by "informed guesswork" on the part of the expert clinician. With our diagnostic test, we believe that the time taken to perform this most necessary trial-and-error process could be reduced from 3 weeks to just 7 days.

For patients with CF, infection leads to inflammation of the lung and the greater the inflammation and time of inflammation, the greater the loss of lung function. Most CF patients suffer 4 infections each year and can spend 50% of their time in hospital. This could be reduced through the use of our new multi-marker test.

Many hospital admissions would be avoided if there was a rapid and accurate assessment of individuals with bacterial infections. One of the major difficulties when assessing patients with respiratory infections is to distinguish bacterial from viral infections. Clinical features are frequently misleading and many patients subsequently admitted to hospital had encountered delays in receiving antibiotics in the community. In the USA approx 1-in-18 or 5.51% or 15 million people per year have misdiagnosed lower respiratory tract infections.

Moreover, primary healthcare workers also face the dilemma of selecting appropriate antibiotics. While empirical antibiotic selection usually results in satisfactory treatment, the ability to identify the level of threat to a vulnerable patient posed by an identified pathogen, would permit optimised antibiotic usage. This would result in: improved early treatment success thereby preventing clinical deterioration and subsequent hospital admission, and reduced use of broad spectrum antibiotics.

SUMMARY OF THE INVENTION

According to a first aspect of the present invention, there is provided a method of determining a level of activity of bacteria in the lung of a patient, the method comprising:
  making a first measurement at a first time of a level of at least one marker of a bacterial iron scavenging process and of at least one secreted bacterial protein in a sample of sputum from the lung;
  making a second measurement at a second time of the levels of said marker and said toxin in a sample of sputum from the lung; and
  determining said level of bacterial activity from changes in said measured levels of said marker of a bacterial iron scavenging process and said secreted bacterial toxin over time.

We have determined, surprisingly, that changes in levels of markers of bacterial iron scavenging processes, such as siderophores, can be predictive of exacerbations, but not in all patients. Similarly, changes in bacterial toxin levels can also be predictive in some patients. A reliable test can be obtained by combining the two measurements as described herein. Further, due to individual patient variability, it is desirable to measure changes over time rather than absolute levels at a single time point; some patients may live with higher background levels than others, and so it is the changes which are diagnostic.

*P. aeruginosa*, like other pathogens, requires Fe (III) ions to survive. The lungs of CF patients typically produce large amounts of mucus, but also leak blood into the fluid-coated air spaces of the lungs. This serves as an iron source for the pathogen. *P. aeruginosa* has multiple mechanisms whereby Fe (III) may be scavenged, and appears to change from one mechanism to another depending on the condition of the host. However, we believe that it is possible to use levels of markers of iron scavenging processes as markers of bacterial activity.

Preferably the marker of an iron scavenging process is a marker of an Fe (III) scavenging process.

Preferably the marker of an iron scavenging process is a siderophore. In preferred embodiments, the siderophore may in particular include one or more of: pyochelin, pyoverdin and pyocyanin.

The marker is a bacterial marker, although in certain embodiments markers of host iron scavenging processes may also be detected. In healthy patients, Fe (III) ions are scavenged by the host (e.g., by lactoferrin, ferritin, or transferrin) to prevent free Fe (III) accumulating which would serve as a reservoir for bacterial growth. Thus the presence of host markers may be useful as an additional marker for determining bacterial activity.

The secreted bacterial protein is preferably a toxin, and may be exotoxin A. Alternatively, the secreted protein may be elastase or alkaline protease or indeed, any protein secreted by the bacterium.

In a preferred embodiment, the combination of pyoverdin and exotoxin A are detected.

The method preferably further comprises measuring at least one additional marker. The additional markers may be selected from bacterial toxins, host iron scavenging markers, bacterial iron scavenging markers, and host inflammatory markers. We believe that detecting a combination of additional markers provides greater sensitivity, accuracy and reliability to the assay than detecting the combination only of markers of iron scavenging and secreted toxins. In a particularly preferred embodiment, the combination of a bacterial toxin, a bacterial marker of iron scavenging process, and a host marker of an iron scavenging process are detected. For example, exotoxin A, a siderophore, and haem or a haem breakdown product may be detected.

The inflammatory marker may be a cytokine.

The bacteria may be *P. aeruginosa*. In certain embodiments, the marker has a concentration dependent on a level of quorum signalling between *P. aeruginosa* bacteria.

The patient may be a patient with cystic fibrosis. In other embodiments, the patient may be a patient with a chronic lung condition, for example, Chronic Obstructive Pulmonary Disease (COPD).

The method may further comprise measuring the level of a plurality of markers of iron scavenging processes and determining the level of bacterial activity from the plurality of measured levels; the markers may be bacterial markers, host markers, or a combination of both.

The method may further comprise measuring the level of at least one iron (III) sequestration intermediate for determining said level of bacterial activity.

The method may further comprise the step of making additional measurements at further time points.

In a further aspect, the present invention provides a method of predicting an exacerbation of a level of bacterial activity in the lung of a patient, the method comprising making a time series of measurements of bacterial activity on said patient using a method comprising making a measurement of a level of at least one bacterial marker of an iron scavenging process and of at least one secreted bacterial protein in a sample of sputum from the lung; and determining said level of bacterial activity from said measured level of said marker of an iron scavenging process and of said protein;

and using said time series of measurements to predict said exacerbation.

A still further aspect of the present invention provides a method of determining the effectiveness of a treatment of a bacterial lung infection, the method comprising making a time series of measurements of bacterial activity on said patient using a method comprising making a measurement of a level of at least one bacterial marker of an iron scavenging process and of at least one secreted bacterial protein in a sample of sputum from the lung; and determining said level of bacterial activity from said measured level of said marker of an iron scavenging process and of said protein;

and determining said effectiveness from a time profile of said level of bacterial activity.

Preferably the treatment is an antibiotic treatment. Preferably the method comprises determining that said antibiotic treatment is ineffective if said level of bacterial activity does not fall with time.

A further aspect of the invention provides a device for use in any of the methods of the invention, the device comprising:
means for collecting said sample of sputum;
means for making a measurement of levels of at least one bacterial marker of an iron scavenging process and of at least one secreted bacterial protein in said sample.

The device may further comprise means for determining said level of bacterial activity from said measured levels of said at least one marker of said iron scavenging process and said protein.

The means for making a measurement of levels may include a reagent which binds to the relevant marker and a reagent which binds to the relevant protein. For example, the reagents may comprise antibodies. The device may comprise a lateral flow strip including said reagents; and may further comprise a colour change marker to indicate the levels of said marker and/or protein.

DETAILED DESCRIPTION OF THE INVENTION

The natural habitat for the *P. aeruginosa* bacterium is not in human hosts—it lives in water and survives in a planktonic state (free cells in water) in rivers and in soil. It can thrive in this environment because it can rapidly adapt and is able to grow on nearly any source of carbon-based foods. Even chemicals toxic to other bacteria such as methanol can be used by this tough pathogen as a carbon source to support growth and replication (1). It adapts quickly under certain conditions, by expressing a wide range of genes associated with metabolism and by deliberately undergoing mutation at a very high rate.

Once established in our lungs (colonisation), *P. aeruginosa* adapts by changing the way it lives. No longer in free suspension in the lungs, this bacterium secretes mucus to form biofilms on the lung surface in which they then hide and protect themselves from the host's own immune defences—and from antibiotics. This makes it largely impossible to remove *P. aeruginosa* once a CF patient has been colonised (usually in their mid teens), which means that this organism stays with the CF patient for the rest of their life, becoming a parasite that frequently threatens the life of the host as it undergoes rapid mutation and evolves into ever more virulent forms.

Recent research in which bacterial DNA isolated directly from sputum was sequenced (and therefore without introducing the bias of subculture), showed that the 10-20 strains present in a single patient all shared the same ancestor and derived from a single clone which then mutated. *P. aeruginosa* therefore undergoes adaptation through mutation, presumably in response to the changes in the host as the patient ages and their lung composition changes over time and as the lung function decreases with each infection-induced inflammation. Each new strain which takes hold probably has a particular advantage over its ancestor that makes it better suited to this ever changing environment.

*P. aeruginosa* appears to live in a form of complex co-operation between cells of the same strain and even between other strains. They have evolved a way of signalling their metabolic status to other cells through a "chemical language". Many chemical signals have been isolated and identified and are collectively called *Pseudomonas* Quorum Signalling (PQS) molecules. These are complex molecular structures and are often insoluble in water which means that they require complex laboratory instrumentation such as LC MS to detect their presence in patient sputum.

Figure 1:
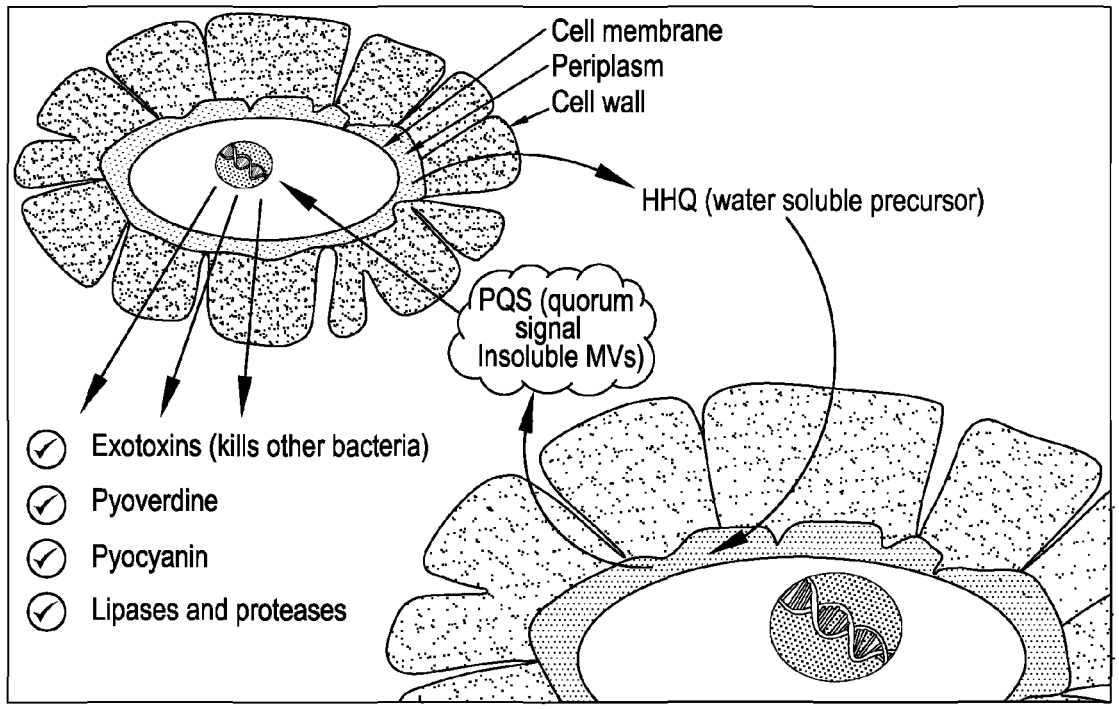
FIG. 1 shows an illustration of quorum sensing in *P. aeruginosa* bacteria. Quorum sensing between bacteria allows cells to communicate chemically. HHQ, the water-soluble precursor of PQS is thought to be assembled in the periplasm (the space between the cell membrane and the cell wall) from components synthesised in the cytoplasm of the cell. HHQ from one cell is acted on by enzymes in the periplasm of a second cell. It is believed that the active molecule, PQS forms vesicles of lipids from the cell membrane of the second cell. When these vesicles interact with the cell membrane of the first cell, it is thought that this provides a signal to start the production of the machinery required for cell growth and replication—in other words, to increase the rate of metabolism. This initiates the production of toxins to kill-off competing bacteria and the mechanisms to scavenge all available free iron (III) ions in the immediate vicinity through the use of siderophores and ferrioxidases. This latter is an enzyme which converts iron (II) into iron (III) that the cell needs.

There are many ideas to explain the purpose of this cell-to-cell signalling, but the most popular theory to explain why cells have developed this capability is that it allows a cell to sense when others around it are increasing their metabolic activity and are about to start a period of rapid multiplication—for the bacterium, this is called Quorum Sensing (FIG. 1). Perhaps the benefit to one strain of the bacterium of being able to sense when the bacterial population is about to increase rapidly, is that each strain can ensure that it is not out-competed for resources by others or that its is not poisoned by the production of exotoxins from another bacterium, by also accelerating its metabolism.

Figure 2:
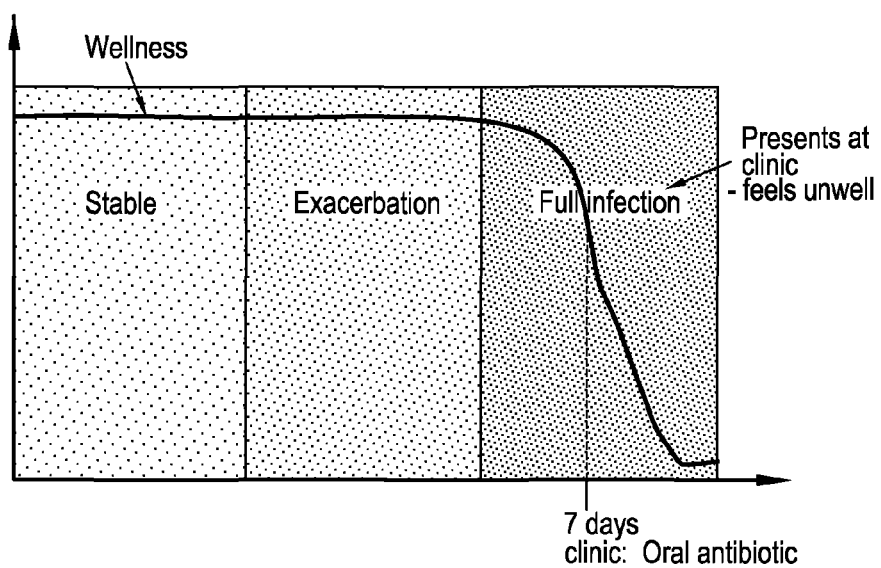
FIG. 2 shows a diagrammatic profile of the phases of infection in a CF patient and their feeling of wellness. The patient usually only presents at the clinic when the exacerbation has progressed into a full-blown infection.

For the bacterium, Quorum Sensing precedes rapid multiplication. For the patient, Quorum Sensing precedes an exacerbation. The trigger causing this change in the bacterium's state from being subdued to highly active is unknown—perhaps through a viral infection or some other change in the health of the patient host. But once it begins and if left untreated, an exacerbation will develop into a full-blown infection within 2-4 days and often before the patient feels unwell (FIG. 2).

The patient's response to an exacerbation can also include an inflammatory response, which can be as damaging to the patient's lungs as the infection itself. This provides another set of biomarkers which may be followed to objectively assess the wellness state of the CF patient.

So knowing when to treat a CF patient with antibiotics so as to control an exacerbation before it develops into a full infection, even before the patient feels unwell, could reduce the severity of infection each time it happened. Also knowing when to intervene through the application of antibiotics is a challenge for both the clinicians and for the CF patient. Overprescription of antibiotics leads to the bacteria becoming resistant to antibiotics by evolving this ability sooner. For CF patients, there are only 2 or 3 antibiotics useful in quelling a full-blown lung infection—and so these medicines have to be prescribed only when essential. This means they cannot be given as a prophylactic and taken continuously, as this would only bring forward the time at which this pathogen develops the capability to tolerate them.

There are few objective measures of wellness for a CF patient as an exacerbation event may be underway without the patient feeling ill. Classical methods used for the non-quantitative monitoring of lung infections are: listening to breath sounds, X-rays and ultrasound and the appearance of and culture of sputum (a mixture of mucus, debris and cells expelled by the lungs). Clinical staff experienced in supporting CF patients have also become adapt at assessing the status of a patient by observing the volume, viscosity and colour of a patient's sputum. The ability to make such subjective observations is acquired from years of experience on the ward—a highly specialised skill which also requires the patient to be at the clinic.

The unmet clinical need is for a rapid, portable, simple and low cost test which is able to quantitatively measure "markers of exacerbation" in sputum, the concentration of which can be used to detect an exacerbation before the full infection takes hold. The detection of *P. aeruginosa* itself is of no benefit as it is always present in most CF patients. For example, detecting the presence of *P. aeruginosa* by qRT PCR is highly sensitive and quantitative for mRNA but this does not correlate to the extent of sepsis, only the presence of the bacterium—and is too expensive and complex to be used in a home environment anyway. What is needed is the ability to detect the change in metabolic status of this bacterium before an exacerbation converts into an infection, by following the concentration of markers longitudinally in a patient over time.

Aspects of the present invention provide a very simple multiple marker process which has not yet been applied in this field: Combinations of any or all of the following markers may be used; in certain embodiments, a single marker—preferably a marker of an iron scavenging process—may be used as an initial diagnostic. The markers are as follows:

Marker 1—detect the toxins produced (e.g. Exotoxin A) as these are simple to test for using a low cost immunoassay. Exotoxin A is produced by *P. aeruginosa* when it is highly active and it secretes these complex molecules as natural poisons to kill-off other bacteria and so gain an advantage in the competition for resources for its own growth. Exotoxin A is also very toxic to the patient, causing symptoms of sepsis, with multiple organ damage.

To increase the accuracy of our test, it would also be an advantage to detect other markers in addition to Exotoxin A to quantify the "bacterial load" (an indication of the total amount of bacteria present in the lungs and their activity "status"). The Quorum Signalling molecules which communicate between bacteria would be ideal as this would allow the clinician to "listen into the conversation between cells", but these are water-insoluble and difficult to measure without the use of complex laboratory equipment. So we have to look for some thing else: a secondary marker that is easier to measure but which is closely coupled to Quorum Signalling.

Marker 2. Iron scavenging markers from the pathogen. Despite its resilience, like all living things, *P. aeruginosa* must have iron (III) ions for it to thrive. This need gives us the opportunity to find a new "handle" by which we can assess how active this pathogen is at any given time, in addition to following the production of Exotoxin A. This new handle or biomarker represents Marker 2 in our test—a handle on how active the cell is in gathering iron (III) ions or more properly, biomarkers for the levels of activity of iron (III) sequestration by the bacteria within the lungs.

The lungs of CF Patients produce a lot of mucus but also leak blood into the fluid-coated air spaces of this vital organ. With this plentiful supply of iron (III), *P. aeruginosa* is able to thrive in CF patients (2) and may even be the cause of anaemia in CF patients (3).

*P. aeruginosa* has a multitude of different mechanisms by which it sequesters iron (III) and it appears to change from one mode to another in response to the ever changing condition of the host. It is therefore overly simplistic to select just a single marker and so we will take a multiplexed approach.

Figure 3:
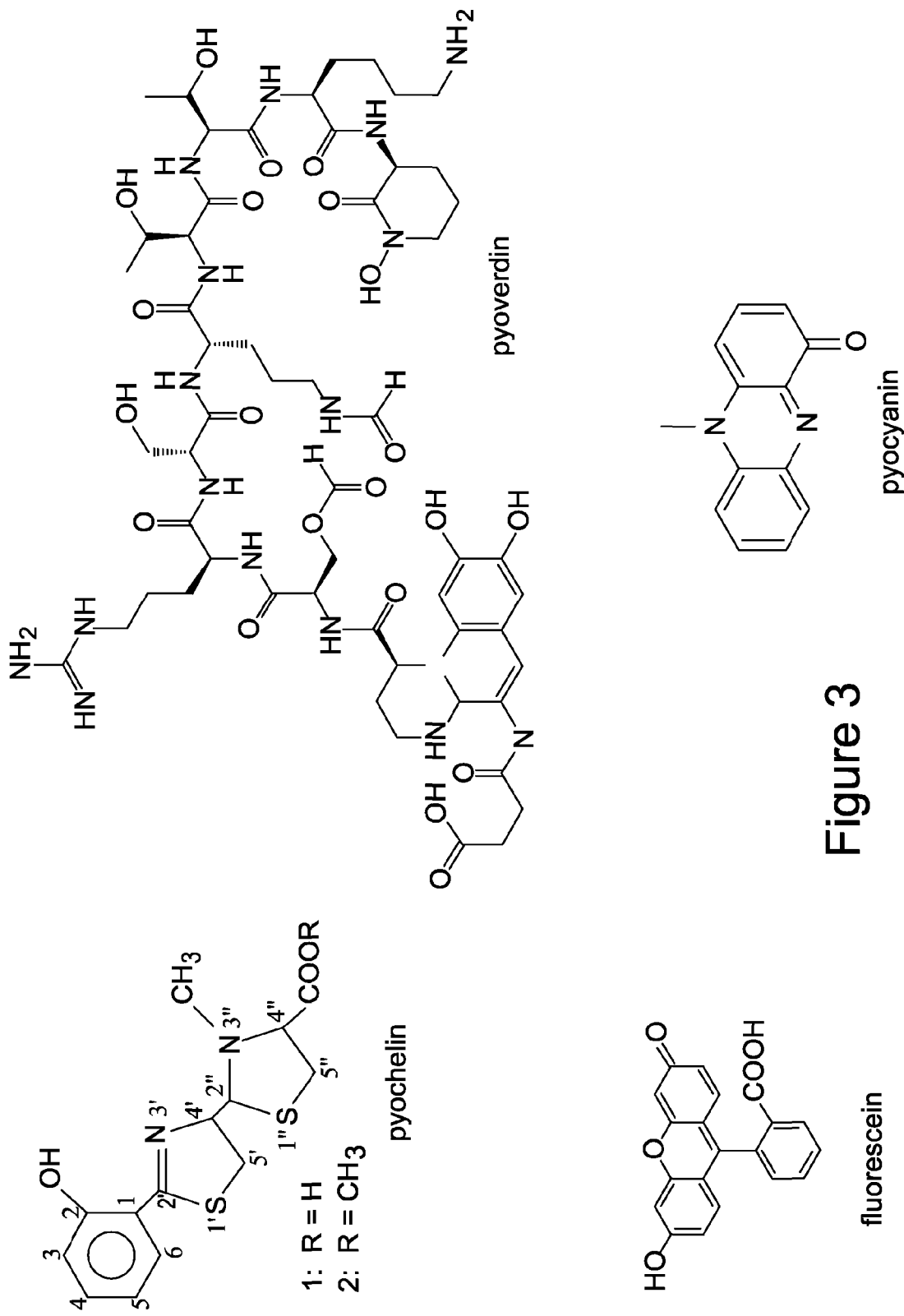
FIG. 3 shows the chemical structure for the siderophores identified from *P. aeruginosa*—just one way in which this pathogen can compete for iron (III). These along with other Iron (III) sequestration intermediates such as Ferrioxidase, could be used to identify exacerbations of infections in patients with CF.

Simple and easy markers for iron (III) sequestration activity assay: The easiest markers to quantify are the bacterial enzyme co-factors or "siderophores" which are produced in copious quantities prior to an exacerbation as a "secondary signal"—that is, they are produced in high concentrations only during periods of active growth. *P. aeruginosa* secretes a variety of pigments, including Pyocyanin (blue-green), Pyoverdin (yellow-green and fluorescent), and Pyorubin (red-brown) (FIG. 3). Under the microscope, *P. aeruginosa* is often preliminarily identified by its pearlescent appearance and grape-like odour. Definitive clinical identification of *P. aeruginosa* often includes identifying the production of both Pyocyanin and Pyoverdin, as well as its ability to grow at 42°.

These siderophores have a very high affinity for the iron (III) ion and are thought to be involved in the mechanism by which these bacteria absorb iron essential for growth (4). The ability to secrete these iron scavengers into the immediate environment around the cell gives the bacterium an advantage in that it can "pick-up and trap" the iron it desperately needs for rapid cell division and protein production. Measuring the concentration of these coloured molecules could be an easy biomarker of iron sequestration activity to profile.

Pyoverdin should be very easy to detect because it is fluorescent—this fluorescence can be quenched by adding iron (III) ions. It can also be detected in sputum using a competition reaction with an iron (III)-binding dye called chrome azurol S (CAS) reagent in a spectrophotometric assay (5). Siderophores could also be detected through the use of an immunoassay, although none have yet been developed. Quantitation of Pyoverdin in sputum using optical detection (absorption or fluorescence) requires extraction with solvents because the thick opaque mucus interferes with the measurement and this does not lend itself to simple devices for home use, but can be used in our laboratory as we perform our initial feasibility tests.

Indeed, Huston et al (6) have already undertaken similar studies in which they found that the concentration of siderophores produced by cultures of bacteria isolated from CF patients and grown in culture media, varied considerably between patients. They profiled the concentration of the siderophores from isolates from a single patient sample then cultured in the laboratory, rather than measuring the concentration of siderophores directly in sputum and then profiling a series of samples from the same patient. Therefore they did not observe the relative changes in concentration for each patient, from a series of samples taken before, during and after an exacerbation. Huston et al, working without the benefit of close co-operation with an expert clinician, concluded that siderophores cannot be used as a biomarker for exacerbation. This approach is flawed and is seen repeatedly in the scientific literature This arises because the biochemists undertaking the research are disconnected from their colleagues in the clinic. Studying the expression patterns of cells grown in the test tube is spurious: we can make these cells do almost anything we want them to by changing their growth conditions, and without the anchor of clinical relevance, this information is of little value in developing clinical tools. These pathogens are adaptable—if the researcher changes their growth media, the cells change their behaviour. What is required is to go directly to the clinical sample and solve the problem of how to measure the markers in sputum rather than to use cultures of cells produced in artificial media.

Huston et al concluded that yet another iron (III) sequestration pathway involving the bacterial enzyme ferrioxidase which is secreted into the periplasm of the bacterium, was the correct biomarker to profile. What these biochemists missed was that it is the total activity of the bacterium in gathering iron (III) that is the best biomarker and this preferably requires a multiplexed approach if we are to create a tool suitable for all patients, with their different strains, all of which are at different stages of evolution within their hosts.

As well as the two preferred markers, toxins and iron scavenging markers, it may be possible to include additional markers in the assay. These include:

Marker 3. Iron scavenging markers by the host. In healthy people, our lungs prevent iron (III) ions from accumulating in the fluid lining lung surfaces so that bacteria cannot take-hold and grow. By absorbing iron (III) ions in number of ways including: the production of iron-binding proteins called lactoferrin, ferritin and transferrin, we protect ourselves by making it scarce to invading pathogens—a very effective form of defence against disease. We also break down haem, the prosthetic group that consists of an iron atom contained in the centre of a large heterocyclic organic ring called a porphyrin. Haems are most commonly seen as components of hemoglobin, the red pigment in blood, but they are also components of a number of other hemoproteins. In competition with bacteria, the host produces the enzyme haem mono oxygenase (aka Ferridoxinase) which breaks down haem into Iron ions (which cannot be absorbed by the bacteria), biliverdin (a yellow pigment) and carbon monoxide. By following the changes in levels of either the enzyme or biliverdin in sputum, we can determine the activity of the host's natural defences against this pathogen.

Marker 4. Inflammatory response: cytokines. Cytokine markers have been reported in the literature extensively. In particular, markers TNFα and IL-8 have already been used to profile patents in our laboratories. Airway disease in cystic is characterised by a continuous cycle of chronic infection and inflammation dominated by a neutrophilic infiltrate. This inflammation is characterised by an increased production of pro-inflammatory cytokines in the lung. The relationship between the abnormal CFTR gene product and the development of inflammation and progression of lung disease in CF is not fully understood. Courtney et al (7) review the mechanisms of pulmonary inflammation in CF, the profiles of cytokines and inflammatory mediators in the lung in CF, and the mechanisms that may predispose to chronic *P. aeruginosa* infection. Imbalances of cytokine secretion are now better understood due to recent advances in understanding CF at a molecular level and it is increasingly thought that the normal inflammatory process is deranged in CF early in the course of the disease and may occur in the absence of detectable infection.

A combination of markers for greater accuracy.

By incorporating assays for bacterial markers for toxin production and iron scavenging, in a simple, multiplexed test, we should be able to accurately assess the metabolic status of *P. aeruginosa* in real-life sputum samples and hence, in the lungs of the patient. Further, by measuring the response by the host in iron scavenging AND cytokine-mediated inflammation, we have another objective means for the determination of the CF patient's status. See table 1.

TABLE 1

Summary of multiple markers useful in the accurate longitudinal profiling of CF patents

| Pathogen | Host |
|---|---|
| Toxin production - Exotoxin A | None |
| Iron scavenging: | Iron scavenging: |
| siderophores | (b) Haem mono oxygenase |
| Haem mono oxygenase | (c) Biliverdin |
| Inflammatory response | Inflammatory response: cytokines |

This approach resolves the low accuracy problem associated with rapid tests for *C. difficile* that is described above.

Indeed, this approach of understanding the metabolic pathways of a pathogen and identifying secondary reporters to be used in combination with the detection of bacterial toxins, can be applied to many different pathogens such as *Staphylococcus aureus*, a second pathogen common in CF patients.

Figure 4:
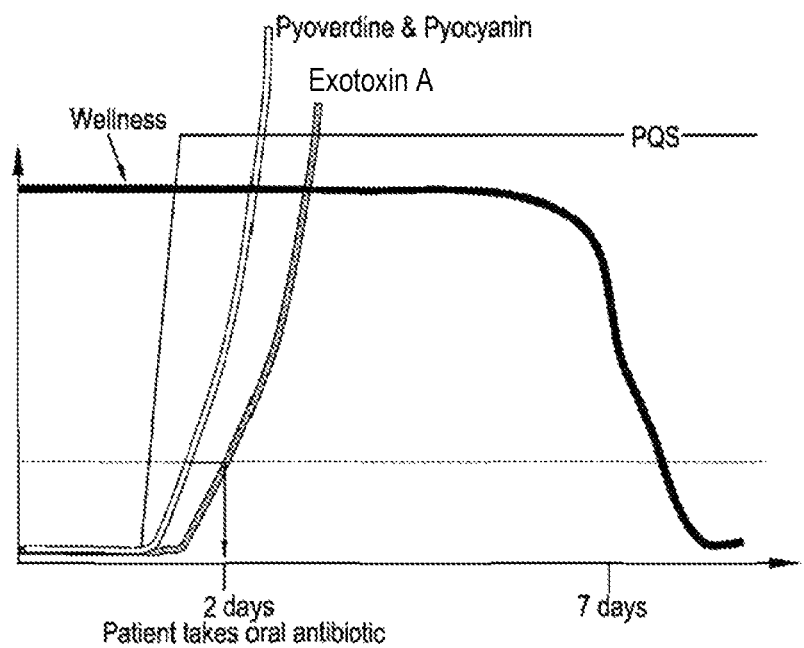
FIG. 4 shows the hypothetical profile of Exotoxin A and Pyoverdin/Pyocyanin/ferrioxidase from *P. aeruginosa*.

Our opinion is that the use of quantitative assays to profile the four classes of biomarker, quantitatively and in longitudinal analysis of each patient, concentration performed on untreated sputum (rather than an invasive blood sample or cells cultured in non-representative growth media) so as to determine the bacterial load of *P. aeruginosa*, is both accurate and sensitive. (FIG. 4).

Our approach of quantifying these smaller biomarkers is far easier to develop and package into a device than the detection of the bacterium itself, which requires proteins or other targets to be released from cells or cell membranes—a more complex and challenging approach to incorporate into an inexpensive home or ward test.

Further, if the combined profile of the four classes of markers in sputum does correlate with lung function performance as we anticipate, we believe we have a simple screening technology that would allow patients to predict an exacerbation, to better manage their condition at home than can be achieved at present and would give healthcare providers a tool with which to make earlier interventions.

Figure 5:
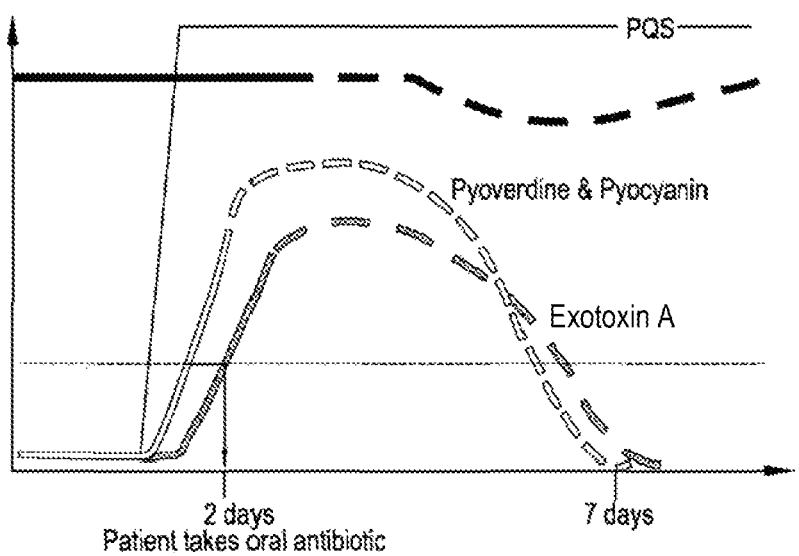
FIG. 5 shows the hypothetical profile of the levels of Exotoxin A and Pyoverdin/Pyocyanin/ferrioxidase compared with patient wellness after administration of the first antibiotic. It could be some days before the patient reports to feeling well and this may not be a good reporter for the efficacy of the drug administered in bringing the infection under control.

A further advantage of embodiments of the present invention is that it would allow clinicians to be able to monitor the effectiveness of the antibiotic treatment within 2-3 day of administration—far faster than current practice. If the bacterial load is decreased following treatment, the antibiotic must be effective and vice versa. Clinical evidence indicates that even when an antibiotic is bringing the infection under control, it may be some days before the patient actually reports that they feel well. The sense of "wellness" may not correlate closely with the performance of the antibiotic being administered in the first and critical days after administration (FIG. 5).

Figure 6:
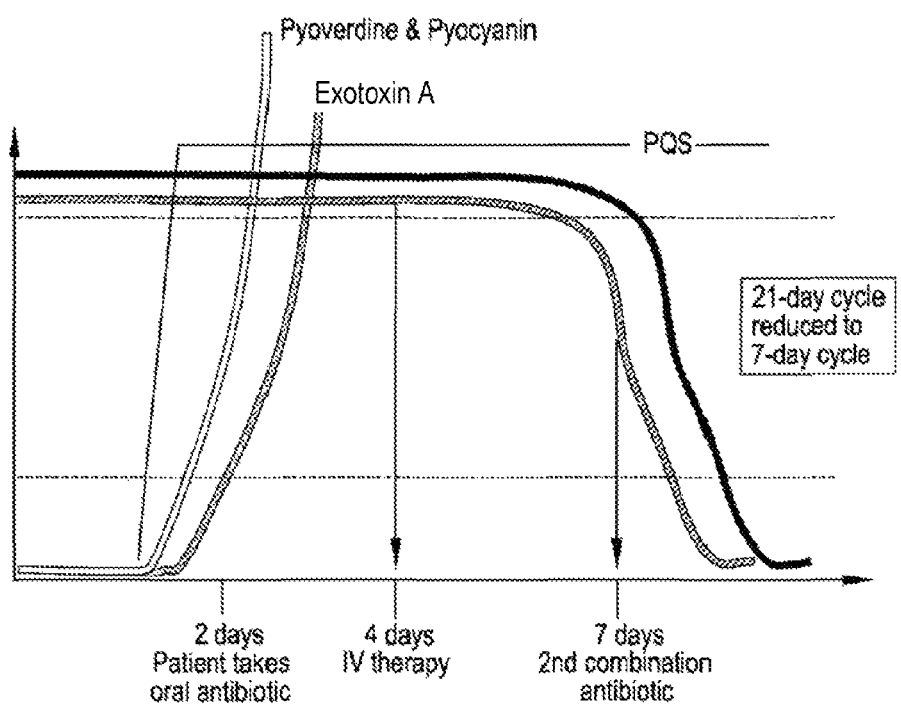
FIG. 6 shows how the present invention may reduce the timelines for the empirical evaluation of the antibiotic options available to the clinician. Our invention could compress a 21-day process into a 7-day process, simply by using a once-a-day disposable test device.

Perhaps the key benefit of our invention for the treating clinician is the ability to objectively monitor the performance of the selected antibiotic, by following the change in concentration of the biomarkers. If the levels of Exotoxin A and Pyoverdin/Pyocyanin/ferrioxidase do NOT fall, this indicates that the antibiotic is not effective. Rather than waiting 7 days to see whether the patient recovers, the Clinician may decide to change to a second antibiotic after just 2 days and so on, until an effective strategy is arrived at. Potentially, this could reduce a 21-day process to a 7-day process, reducing inflammation and thereby saving lung tissue, while reducing hospital admissions and hospital bed occupation (FIG. 6).

Although the present invention may be performed as separate assays on separate sputum samples, it would be more convenient for the user to have the 3 tests performed together on a single "dipstick-type" test, for example.

Figure 7:
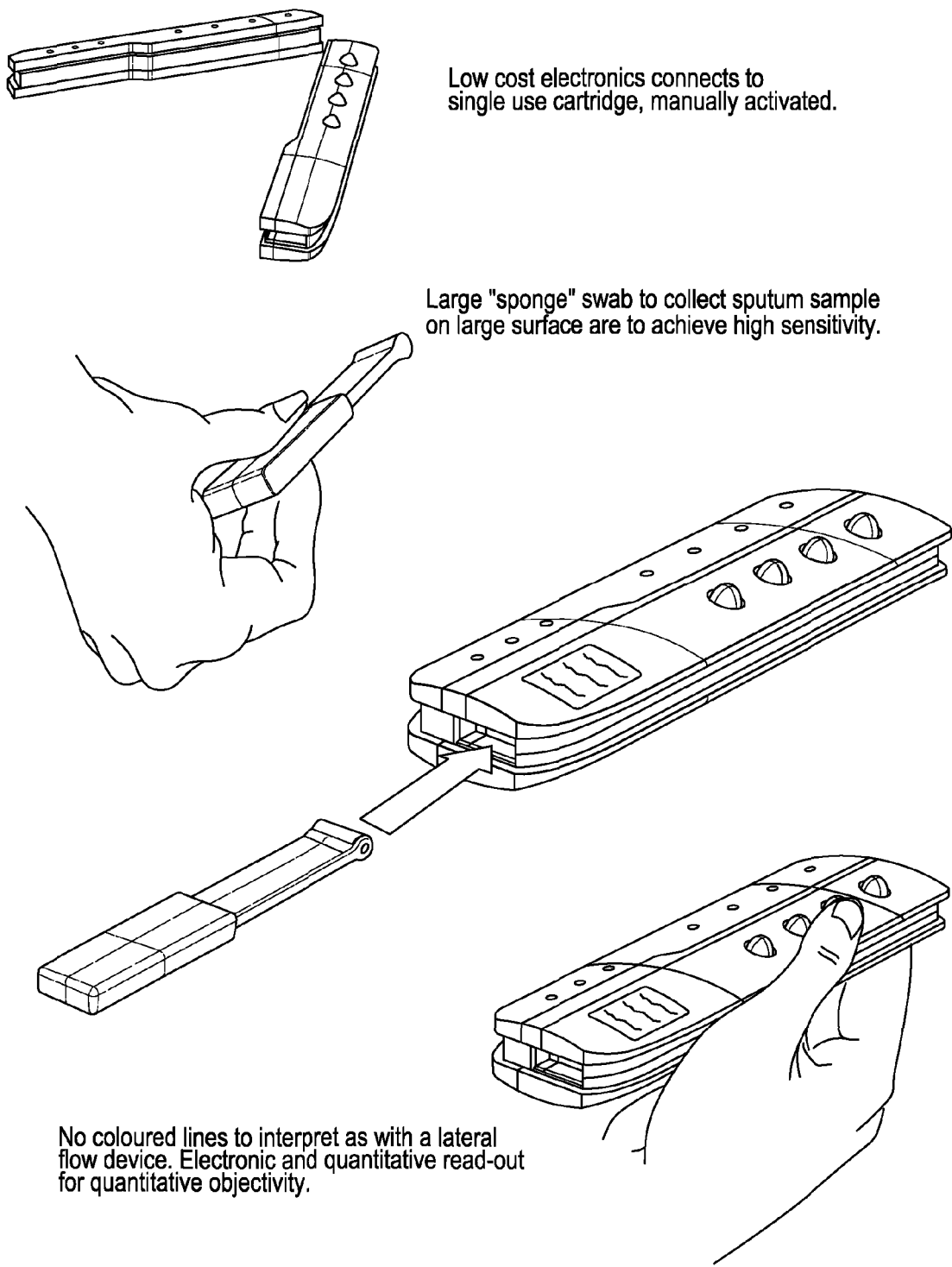
FIG. 7 shows a design concept for a device for use with the method of the present invention.

A design concept for such a single test is shown in FIG. 7. The test may incorporate either a biosensor or lateral flow device. Either approach will require a re-useable electronics element to quantitate the signal generated.

Experimental Data

As a proof of concept of the above, we profiled sputum samples from 5 different patients. For patients colonised with *P. aeruginosa*, an exacerbation of infection was detected by profiling the level of Exotoxin A in sputum 7 or more days before the patient felt so unwell that they presented themselves to the clinic. We have demonstrated that efficacy of treatment with one antimicrobial compared with another, can be determined through longitudinal profiling of Exotoxin A in sputum. We identified two possible fluorescent biomarkers present in sputum. One was confidently identified as a siderophore produced as an iron scavenging and/or quorum sensing molecule by the bacterium. Its production precedes an exacerbation in one patient profiled. The identity of the second molecule is at present unknown. When this second molecule was present in high concentrations, the siderophores produced by the bacteria were not detectable. The presence of these two markers appears to be mutually exclusive. We speculate that this is a compound (or compounds) produced by the host as it was present in the sputa of CF patients who were both positive and negative for *P. aeruginosa*.

We profiled two additional markers for inflammation produced by the host—the cytokines IL8 and TNFα. While useful, inflammatory markers did not appear to be good predictors of an exacerbation—itself highly valuable information—but their levels did show a marked decrease during successful antimicrobial therapy.

Daily sputum samples were obtained from five patients.

Five biomarkers were selected which had the highest chance of being useful in acting as surrogates for the virulence of a colonising pathogen. Virulence is a combination of the amount of bacteria present (the load, not the concentration) and its activity in situ in the lung. We selected as biomarkers molecules which play key roles the bacterium's ability to thrive and multiply or are molecules produced by the host (the patient) in response to infection or as part of their defence against infection.

We were therefore attempting to create "snap-shot pictures" of the situation when the sample was taken.

The biomarkers are listed in table 2 below:

| Pathogen marker | Host marker |
| --- | --- |
| Toxin production - Exotoxin A | None |
| Iron scavenging: | Iron scavenging: |
| Siderophore | Haem mono oxygenase |
| | Biliverdin/bilirubin |
| | Inflammatory response: |
| | Cytokine IL-8 |
| | Cytokine TNF-α |
| | Lactoferrin |

The precedence for the use of bacterial toxins as markers for infection is well established, e.g., *C. difficile* Toxins A and B. The weakness of using any one of these by themselves as sole markers in the detection of *C. difficile* has now been recognised: these rapid POC tests offer an 80-85% accuracy of detection compared with cell culture (which at 78 hours is too slow). Some samples simply do not contain Toxins A/B in detectable amounts and this limits the accuracy of these tests.

By contrast, the use of siderophores (molecules produced by the bacterium which are involved in cell signalling and in scavenging the iron, and so are essential for rapid growth) has been reported as a possible biomarker—with mixed results. Not all of the isolates of *P. aeruginosa* from the sputum of CF patients, produce this fluorescent molecule. Our theory is that as the colonising bacteria mutates over the life of the host, it adapts. As the patient ages and suffers ever greater lung damage and has greater bleeding into the lungs, the need for the bacterium to expend energy in scavenging iron is reduced, and non siderophores-producing clones have a selective advantage. This may explain why some patients have bacterial colonies which lack the ability to produce siderophores—they do not need to as it is metabolically expensive for the bacteria to produce it. So siderophores by themselves are not reliable markers for all patients either. Therefore an approach which exploits a combination of markers of very different processes undertaken by the bacteria is useful and gives greater opportunities to capture an accurate snap-shot, irrespective of the state of mutation of the original wild-type bacterium which colonised the patient in their mid teens.

To protect our lungs from invading pathogens, mammals have evolved mechanisms to remove iron from the mucus which lines the walls of the lung tissue exposed to air. These processes (and there are many) breakdown haemoglobin from blood which may leak into the fluids covering the lung surfaces, into Iron (II) from the Iron (III) form which the bacteria require for rapid growth. This makes the iron unavailable because bacteria cannot uptake iron in the Iron (II) form. The breakdown by-products, catalysed by many enzymes but notably Haem mono oxygenase, result in the production of coloured pigments biliverdin and bilirubin—most usually seen in our bruises. Following the production of these pigments or the activity of the host enzyme which catalyses this process and therefore works to defend us through iron scavenging, is another marker.

Finally, we selected cytokines—small molecules produced by the host as part of an inflammatory response to invading pathogens and their toxins. Cytokines IL8 and TNFα have been detected in the sputum of CF patients by other workers.

Assay Development

All of the assays required similar sample preparation to remove the interfering mucus. We explored several methods to remove this non-homogeneous material, including mechanical breakdown, chemical digestion and separation by ultracentrifugation. A combination of chemical digestion and homogenisation worked well for immunoassay-based tests. This step plus an additional precipitation step of organic molecules (DNA, fats and proteins) was required for the siderophore assay.

IL8 and TNFα:

Assay used was a commercial kit from Millipore using the Luminex immunoassay bead technology. All samples were profiled for these two biomarkers.

Exotoxin A:

In our final Exotoxin A assay, whole sputum was chemically digested and tested "raw" with an immunoassay. We were able to profile patients and demonstrate that Exotoxin A can be used as a marker to predict exacerbation and follow the control of infection after the initiation of antimicrobial therapies.

Siderophores.

Several compounds have been identified and classified as siderophores and have a variety of names including: pyocyanin (blue-green), fluorescein (yellow-green and fluorescent, now also known as pyoverdin), and pyorubin (red-brown). These have characteristic absorption and fluorescence spectra. Previous reports in the literature of the determination of the levels of these in sputum, involved the use of complex chromatographic clean-up processes and/or chemical labelling. These are too expensive for large-scale studies. We developed a very simple method in which these molecules were separated from the mucus, proteins and DNA using a simple single step precipitation with small volumes of solvent which was then removed by evaporation. This simple process could be readily automated. The precipitation step removed the green colouration often associated with samples from infected patients and so the resulting pigments we measured were not proteins such as haemoglobin or alginate, but they were readily soluble in water and organic solvents. These are likely to be organic molecules with polar side groups.

Considerable optimisation of the sample preparation process will be possible in future iterations, but nonetheless and despite these limitations, detection limits for Exotoxin A of 0.1 ng/ml were achieved in whole sputum. Values of 20 ng/ml and above correlated closely with patients becoming ill and requiring treatment with antimicrobials. Upper values of 160 ng/ml in blood have been reported in the literature. There is considerable scope to improve the limits of detection for this assay. With our own reagents and fully optimised sample preparation processes and assays, we anticipate achieving detection limits of 1 ng/ml in a 10 minute test. We forecast that this will enable us to detect Exotoxin A before the patient feels unwell, giving 7-10 days advanced warning of an impending exacerbation.

Results

Figure 8:
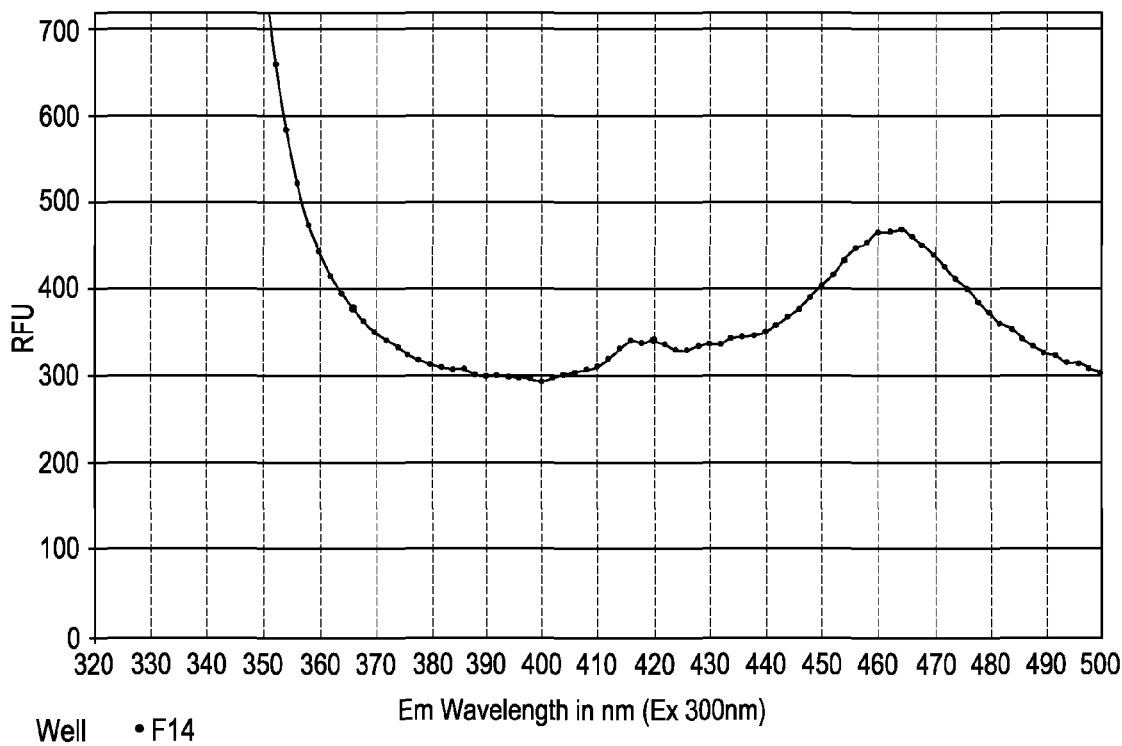
FIG. 8 shows an emission spectrum from a typical patient for detection of siderophores.

Fluorescence spectra were taken for each of the 260 samples to detect and quantify the relative concentration of the siderophores population in sputum. FIG. 8 shows the emission spectrum of extracted fraction from patient sputum typical of siderophores reported in the scientific literature. Excitation was at 300 nm and emission was scanned from 320 nm to 500 nm. Units recorded were Relative Fluorescent Units (RFUs). This spectrum was from a sputum sample taken from Patient 2 towards the end of their profiled period.

Figure 9:
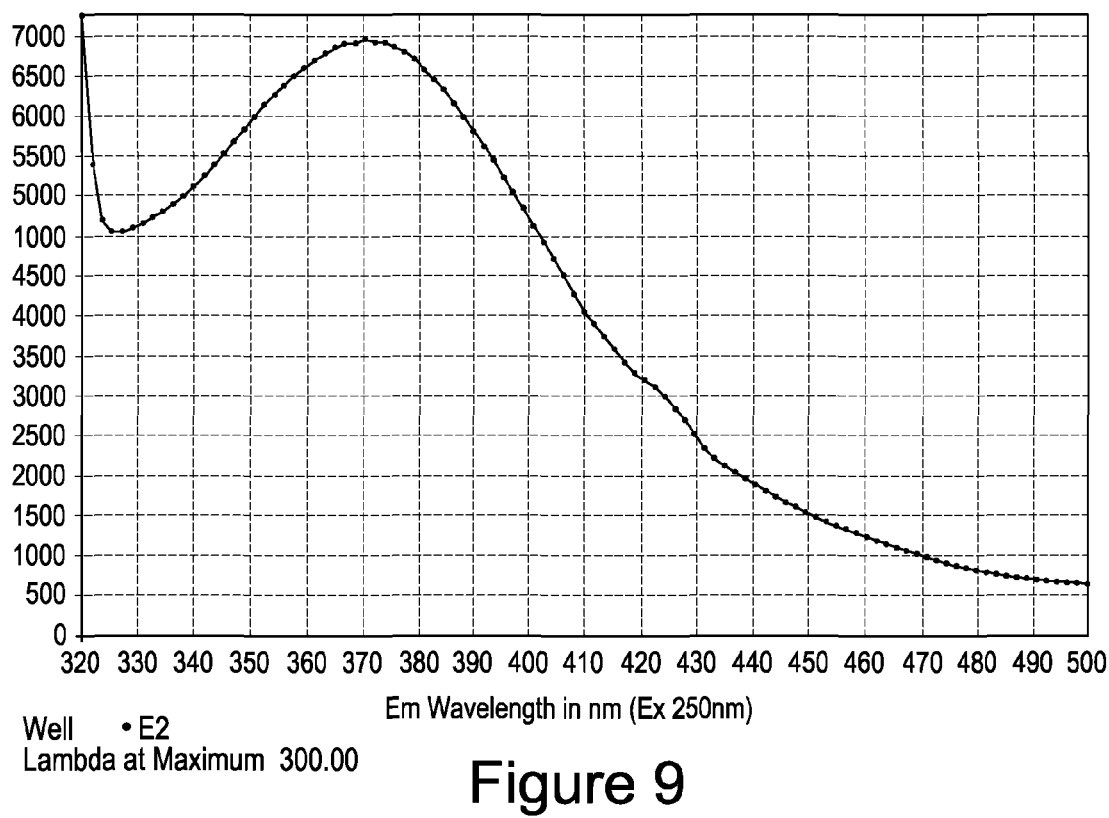
FIG. 9 shows another emission spectrum illustrating the typical peak at 340 nm.

We were also surprised to find another entity with a very distinct spectral fingerprint which had a characteristic peak at 340 nm with an excitation of 280 nm. The concentration of this material in some samples was so high that they appeared orange in colouration. FIG. 9 shows a characteristic peak at 340 nm with an excitation of 280 nm. Note the slight hint of a peak at 410 nm. This spectrum was recorded from Patient 2 at the start of their profiled period. This 340 peak disappeared completely from the sputum of this patient towards the end of their profiled period.

The identity of peak 340 remains unknown, but the spectrum is characteristic of haem breakdown products and suggests that patients with high concentrations of this material are bleeding into their lungs. That this is NOT a product from the pathogen was confirmed when sputum samples from ill CF patients who were negative for *P. aeruginosa* were analysed and found to also contain this peak.

Biomarker Profiles in 5 CF Patients.

We profiled the sputa of 5 patients. Our volunteers were encouraged to give a sample every day; however there were periods during which samples were not collected and so there are gaps in the data.

Values of each biomarker were plotted on charts set to the same scale, to make comparisons between patients easier to make. These plots were then annotated with patient history, recording wellness or illness reports, treatment with oral and IV antimicrobials and admission to clinic.

IL8 and TNFα: the levels expressed varied considerably. In general, levels increased during an excacerbation, but were not predictive of an impending exacerbation. Notably levels of both cytokines decreased during treatment with antimicrobials, especially when the patient was treated in-clinic.

Exotoxin A: two periods for different patients demonstrate proof-of-concept in solving the core problems.

Peak 460: additional biomarker to support Exotoxin A, especially for those enjoying good health for longer periods. Observed in one patient who was well during the profiled period.

Peak 340: useful in assessing the wellness (vulnerability) of patients to exacerbation.

Problem 1: Early warning of exacerbation.

Exotoxin A as Marker.

Figure 10:
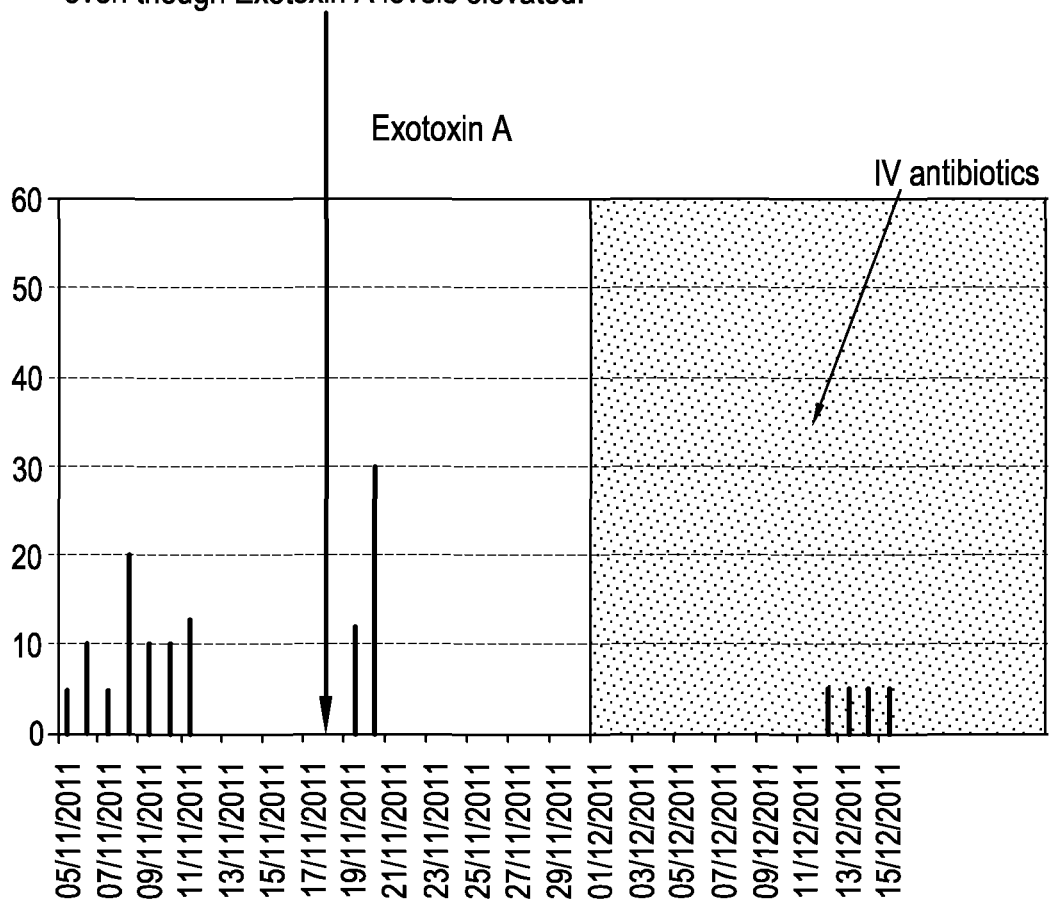
FIG. 10 shows exotoxin A levels over time in patient 5.

Patient 5 showed elevated levels of Exotoxin A but reported as well during routine clinic visit. 14 days later Patient 5 reported as ill and was admitted. FIG. 10 shows this patient's Exotoxin A profile. Values elevated prior to visit to clinic where they reported as well. Levels continued to rise. 14 days later Patient 5 reported as unwell and IV antibiotics were administered. Levels of Exotoxin A fall during IV treatment.

Siderophore as Marker.

Figure 11:
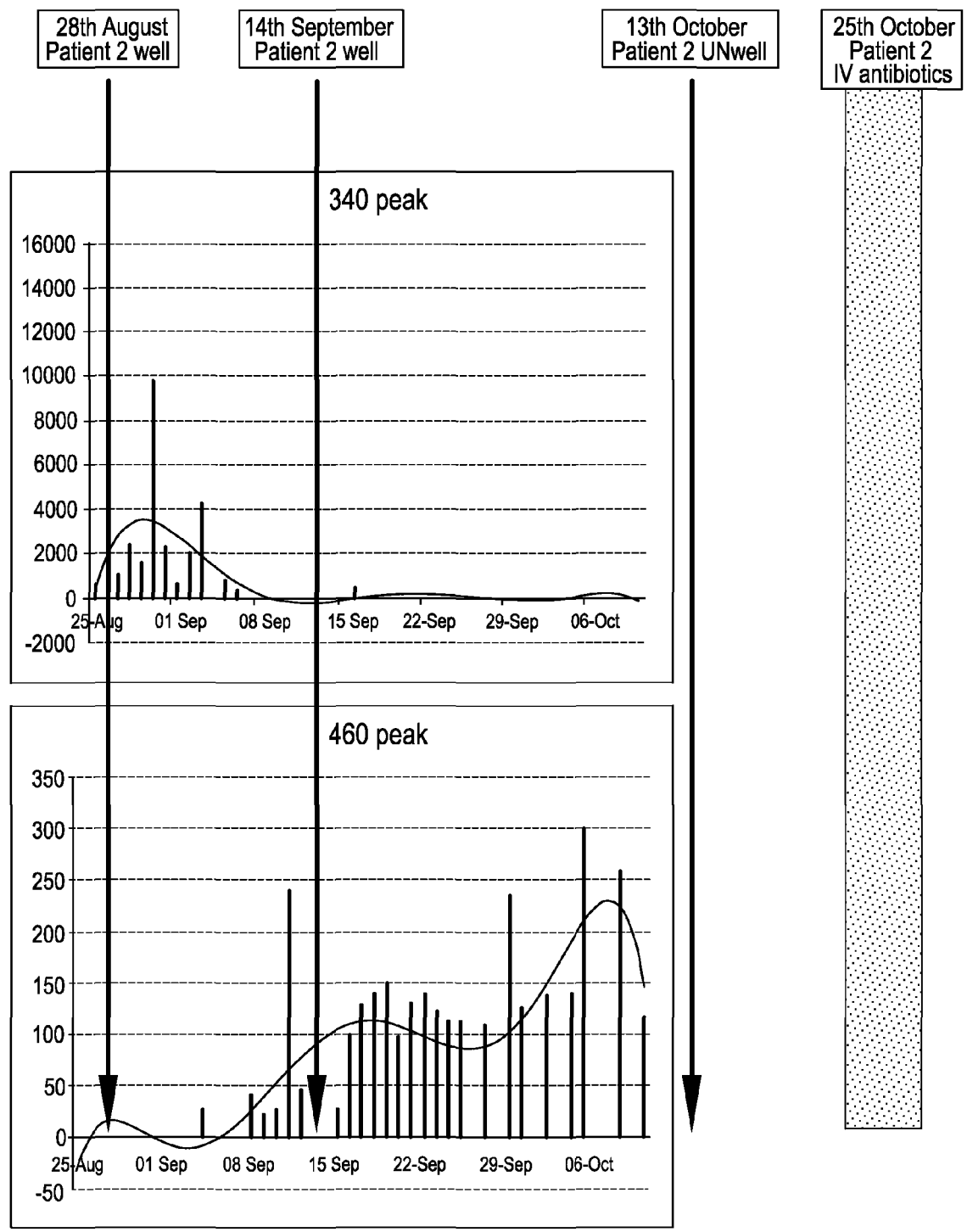
FIG. 11 shows 340 nm and 460 nm emission peaks over time in patient 2.

Patient 2 showed presence of 340 peak at start of profiling period. These levels fell to zero with the concomitant increase in the 460 peak. The patient reported as ill 5 days later. IV antimicrobials administered 10 days after this. FIG. 11 shows the results from this patient.

Problems 2 & 3: Early decision-making about the effectiveness of an antimicrobial therapy and objective feedback about the quality of self-management at home.

Figure 12:
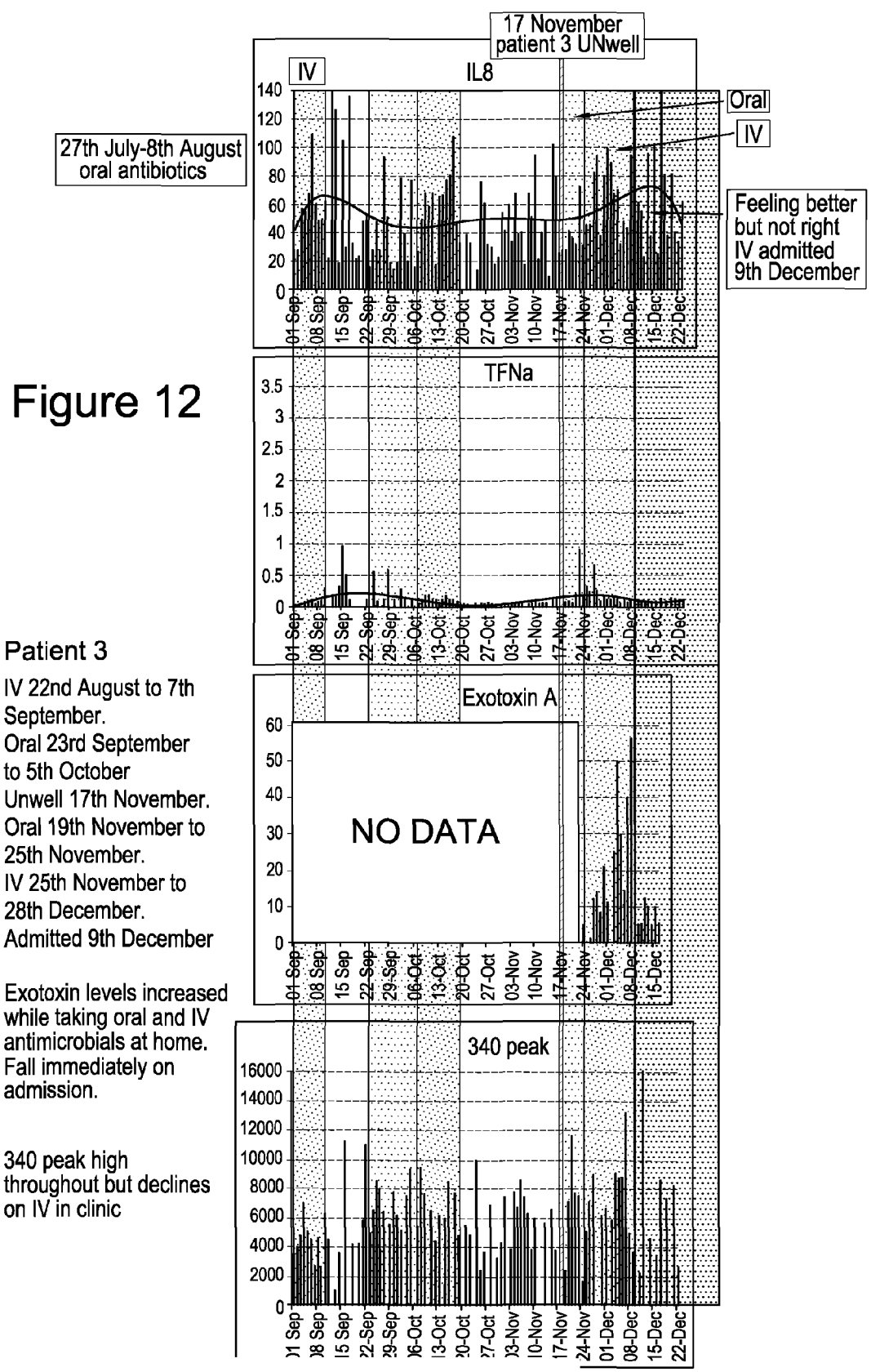
FIG. 12 shows exotoxin, siderophore, and inflammatory marker levels over time in patient 3.

Patient 3 provided samples spanning one period of oral antibiotic treatment, three periods of IV treatment and admission to clinic. There is a wealth of information which is summarised in FIG. 12.

Figure 13:
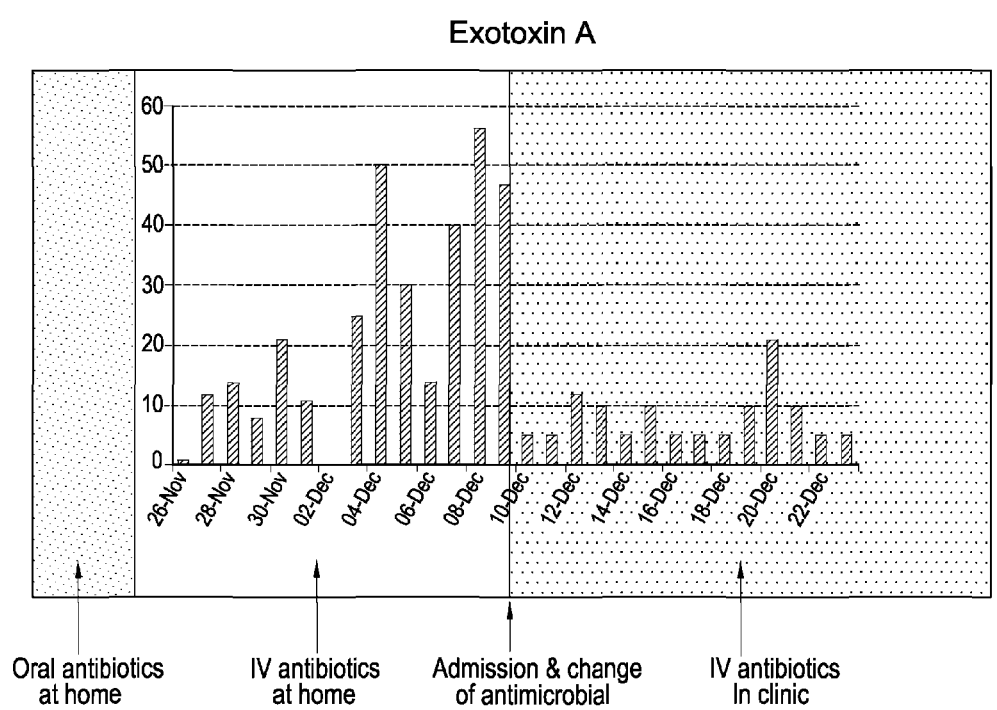
FIG. 13 shows exotoxin A levels over time in patient 3.

Exotoxin A:

Patient 3 became unwell on the 17$^{th}$ November and began oral antimicrobials on the 19$^{th}$ November (see FIG. 13). Treatment was changed to IV antimicrobials on the 25$^{th}$ November. Levels of Exotoxin A continued to rise while on IV treatment at home. Patient 3 reported "feeling better but not right" and was admitted on the 9$^{th}$ December. Once In clinic, treatment was changed to an alternative antimicrobial. Levels of Exotoxin A decreased to baseline immediately.

Peaks 340 and 460:

Patient 3 showed elevated levels of the 340 peak throughout. No 460 peak was detected. This was a common theme for all patients with the exception of Patient 2. With the exception of Patient 2 (21 year old male), all were ill and being treated with antimicrobials during their profile period including Patient 4 (21 year old female twin of Patient 2). These patients were selected for this study because they are regularly ill. We associated high levels of peak 340 over a long duration with patients being ill—perhaps at risk of exacerbation or prone to exacerbation. Patient 3 fits this hypothesis.

Conclusions from Profiling.

Longitudinal profiling of sputum from CF patients—an easily available body fluid and therefore more likely to enjoy patient compliance to a testing regime—can solve Problems 1, 2 and 3 (unmet needs):

Exotoxin A profiling can be used to predict exacerbations by 7+ days as demonstrated by patients 3 and 5.

Siderophores cannot be detected in all patients, especially those consistently ill. But for those who are well (and therefore not showing peak 340), it could be a useful co-marker to Exotoxin A (Patient 2)

Peak 340 and peak 460 are mutually exclusive (Patient 2).

Younger patients (2 and 4 who are twins) have similar (and low) concentrations of peak 340, while the other older patients have high levels which remain consistently high throughout. We associate consistent levels of peak 340 with regular illnesses.

Exotoxin A can be used as a marker for the efficacy of antimicrobial therapies. The example of Patient 3 in which a change in treatment brought about overnight reduction in levels is compelling.

Cytokine levels fall during treatment but may show a too generalised response to be used in profiling for the purpose of solving problems 1-3.

In conclusion, an ideal test would be a combination of lateral flow devices, one for Exotoxin A, one for peak 340 compound(s) and one for siderophores (peak 460 compounds). Patients with consistently high 340 peak compounds would be deemed to be vulnerable to exacerbation and monitored closely. Any increase in these patients' Exotoxin A levels would trigger the immediate administration of oral antimicrobials (Day 1) and twice daily testing. Failure to reduce levels would trigger the administration of IV antimicrobials at home (Day 3). Failure to reduce levels would instigate treatment in clinic, perhaps with an alternative antimicrobial (Day 5). Once in clinic, Exotoxin A tests would confirm the efficacy of the selected treatment and would provide reassurance that the infection was under control, giving confidence for the early release of the patient to home care. On-going treatment at home would be monitored and any relapse (due to poor self administration of medication, for example) would be signalled by increased Exotoxin A levels.

REFERENCES

1. Auton, K. Ph.D Thesis 1988. Southampton University
2. Lamont I L, Konings A F, Reid D W. Biometals. 2009 February; 22(1):53-60. Epub 2009 Jan. 7
3. Reid D W, Withers N J, Francis L, Wilson J W, Kotsimbos T C, Chest. 2002 January; 121(1):48-54
4. Haas, Kraut, Marks, Zanker, Casignetti INFECTION AND IMMUNITY, November 1991, p. 3997-4000
5. Schwyn B, Neilands J B. Anal Biochem. 1987 January; 160(1):47-56
6. Huston, Potter, Jennings, Rello, Hauser, McEwan. J Clin Microbiol. 2004 June; 42(6): 2806-2809.
7. Courtney, J M, Ennis, M and Elborn, J S. Journal of Cystic Fibrosis Volume 3, Issue 4, Pages 223-231, December 2004

The invention claimed is:

1. A method of predicting an exacerbation of a level of *Pseudomonas aeruginosa* bacterial activity in the lung of a patient, the method comprising:
    making a time series of measurements of bacterial activity on the patient using a method comprising:
        making a first measurement at a first time of a level of at least one marker of a bacterial iron scavenging process and of at least one secreted bacterial protein in a sample of sputum from the lung of the patient;
        making a second measurement at a second time of the levels of the at least one marker and the at least one secreted bacterial protein in a sample of sputum from the lung of the patient; and
        determining the level of bacterial activity from changes in the measured levels of the at least one marker and the at least one secreted bacterial protein over time; and using the time series of measurements to predict the exacerbation.

2. The method of claim 1 comprising measuring the level of a plurality of markers of bacterial iron scavenging processes and determining the level of bacterial activity from the plurality of measured levels.

3. The method of claim 1, wherein the at least one marker of a bacterial iron scavenging process comprises a siderophore.

4. The method of claim 1, further comprising measuring the level of at least one iron (III) sequestration intermediate for determining the level of bacterial activity.

5. The method of claim 1, wherein the at least one secreted bacterial protein comprises a bacterial toxin.

6. The method of claim wherein the at least one marker of a bacterial iron scavenging process comprises pyochelin, pyoverdin, or pyocyanin.

7. The method of claim 1, wherein the at least one marker comprises pyoverdin and the at least one protein comprises exotoxin A.

8. The method of claim 1, further comprising determining the effectiveness of an antibiotic treatment of a *Pseudomonas aeruginosa* bacterial lung infection based on the time series of measurements of bacterial activity from the patient, wherein the patient is undergoing the antibiotic treatment of a lung infection.

9. The method of claim 8 further comprising determining that the antibiotic treatment is ineffective if the level of bacterial activity does not decrease with time.

10. The method of claim 8, further comprising determining that the antibiotic treatment is effective if the level of bacterial activity decreases with time.

11. The method of claim 1, wherein the at least one marker has a concentration dependent on a level of quorum signalling between the *P. aeruginosa* bacteria.

12. The method of claim 1 further comprising the step of detecting a host marker of an iron scavenging process.

13. The method of claim 12, wherein the host marker of an iron scavenging process comprises haem or a haem breakdown product.

14. The method of claim 1 further comprising measuring the level of an inflammatory response of the patient.

15. The method of claim 1, wherein the at least one secreted bacterial protein comprises a bacterial toxin, and wherein a host marker of an iron scavenging process is also detected.

16. The method of claim 15, wherein the at least one secreted bacterial protein comprises exotoxin A, wherein the at least one marker comprises a siderophore, and wherein the host marker comprises haem or a haem breakdown product.

17. The method of claim 1, wherein the at least one secreted bacterial protein comprises exotoxin A.

18. The method of claim 1, wherein exacerbation is predicted by increased levels of the at least one marker and the at least one secreted bacterial protein over time.

* * * * *